United States Patent
Zilberstien et al.

(10) Patent No.: US 10,991,095 B2
(45) Date of Patent: Apr. 27, 2021

(54) SYSTEMS AND METHODS FOR COMPUTATION OF FUNCTIONAL INDEX PARAMETER VALUES FOR BLOOD VESSELS

(71) Applicant: Spectrum Dynamics Medical Limited, Road Town (VG)

(72) Inventors: Yoel Zilberstien, Herzlia (IL); Nathaniel Roth, Tel-Aviv (IL); Olga Denisova, Haifa (IL)

(73) Assignee: Spectrum Dynamics Medical Limited, Road Town (VG)

( * ) Notice: Subject to any disclaimer, the term of this patent is extended or adjusted under 35 U.S.C. 154(b) by 47 days.

(21) Appl. No.: 16/466,051

(22) PCT Filed: Jan. 23, 2018

(86) PCT No.: PCT/IB2018/050404
§ 371 (c)(1),
(2) Date: Jun. 3, 2019

(87) PCT Pub. No.: WO2018/138635
PCT Pub. Date: Aug. 2, 2018

(65) Prior Publication Data
US 2019/0355118 A1   Nov. 21, 2019

Related U.S. Application Data

(60) Provisional application No. 62/449,614, filed on Jan. 24, 2017.

(51) Int. Cl.
*G06T 7/00* (2017.01)
*G16H 10/60* (2018.01)
(Continued)

(52) U.S. Cl.
CPC ............ *G06T 7/0012* (2013.01); *A61B 6/032* (2013.01); *A61B 6/037* (2013.01); *A61B 6/481* (2013.01);
(Continued)

(58) Field of Classification Search
CPC .. G06T 7/0012; G06T 11/003; G06T 2111/10; G06T 2207/10088;
(Continued)

(56) References Cited

U.S. PATENT DOCUMENTS

| 2014/0005535 A1 | 1/2014 | Edic et al. |
| 2014/0058715 A1 | 2/2014 | Sharma et al. |

(Continued)

FOREIGN PATENT DOCUMENTS

| EP | 2633815 | 9/2013 |
| WO | WO 00/57777 | 10/2000 |

(Continued)

OTHER PUBLICATIONS

International Preliminary Report on Patentability dated Aug. 8, 2019 From the International Bureau of WIPO Re. Application. No. PCT/IB2018/050404. (9 Pages).

(Continued)

*Primary Examiner* — Khai M Nguyen

(57) ABSTRACT

There is provided a method for calculation of a functional index parameter in at least one blood vessel of a patient, comprises: receiving a dataset of registered functional image data and anatomical image data, wherein the functional image data and the anatomical image data include data indicative of anatomical and functional data for at least one blood vessel of a certain patient; calculating at least one value for at least one functional index parameter for at least one of: (i) at least one blood vessel, and (ii) for the anatomical region of the at least one blood vessel, wherein (Continued)

the at least one value of the at least one functional index parameter is computed based on the functional image data of the dataset; and outputting the calculated at least one value for the at least one functional index parameter for the at least one blood vessel of the certain patient.

19 Claims, 7 Drawing Sheets

(51) Int. Cl.
G16H 50/30 (2018.01)
G16H 50/20 (2018.01)
G16H 30/40 (2018.01)
A61B 6/03 (2006.01)
A61B 6/00 (2006.01)
G06T 11/00 (2006.01)
G06F 30/20 (2020.01)
G06F 111/10 (2020.01)

(52) U.S. Cl.
CPC .............. A61B 6/504 (2013.01); A61B 6/507 (2013.01); A61B 6/5217 (2013.01); A61B 6/5247 (2013.01); G06F 30/20 (2020.01); G06T 11/003 (2013.01); G16H 10/60 (2018.01); G16H 30/40 (2018.01); G16H 50/20 (2018.01); G16H 50/30 (2018.01); G06F 2111/10 (2020.01); G06T 2207/10088 (2013.01); G06T 2207/10104 (2013.01); G06T 2207/10108 (2013.01); G06T 2207/10116 (2013.01); G06T 2207/30104 (2013.01)

(58) Field of Classification Search
CPC . G06T 2207/10104; G06T 2207/10108; G06T 2207/10116; G06T 2207/30104; G16H 10/60; G16H 50/30; G16H 50/20; G06F 30/20; A61B 6/032; A61B 6/037; A61B 6/481; A61B 6/504; A61B 6/507; A61B 6/5217; A61B 6/5247
See application file for complete search history.

(56) References Cited

U.S. PATENT DOCUMENTS

2014/0107935 A1 4/2014 Taylor
2017/0039706 A1* 2/2017 Mikhno ................. G06T 15/08
2020/0085502 A1* 3/2020 Taylor ................ A61B 5/02028

FOREIGN PATENT DOCUMENTS

WO WO 2014/091339 6/2014
WO WO 2015/134662 9/2015
WO WO 2018/138635 8/2018

OTHER PUBLICATIONS

International Search Report and the Written Opinion dated May 18, 2018 From the International Searching Authority Re. Application No. PCT/IB2018/050404. (18 Pages).
Johnson et al. "Clinical Evaluation of a New Concept: Resting Myocardial Perfusion Heterogeneity Quantified by Markovian Analysis of PET Identifies Coronary Microvascular Dysfunction and Early Atherosclerosis in 1,034 Subjects", The Journal of Nuclear Medicine, XP055381383, 46(9): 1427-1437, Sep. 2005.
Knaapen et al. "Coronary Microvascular Resistance: Methods for Its Quantification in Humans", Basic Research in Cardiology, XP019739749, 104(5): 485-498, Published Online May 26, 2009.
Communication Pursuant to Article 94(3) EPC dated Sep. 11, 2020 From the European Patent Office Re. Application No. 18705729.4. (3 Pages).

* cited by examiner

# SYSTEMS AND METHODS FOR COMPUTATION OF FUNCTIONAL INDEX PARAMETER VALUES FOR BLOOD VESSELS

RELATED APPLICATIONS

This application is a National Phase of PCT Patent Application No. PCT/IB2018/050404 having International filing date of Jan. 23, 2018, which claims the benefit of priority under 35 USC § 119(e) of U.S. Provisional Patent Application No. 62/449,614 filed on Jan. 24, 2017. The contents of the above applications are all incorporated by reference as if fully set forth herein in their entirety.

BACKGROUND

The present invention, in some embodiments thereof, relates to methods and systems for computation of a functional index parameter and, more specifically, but not exclusively, to methods and systems for computation of a functional index parameter of blood vessel(s) of a patient.

A stenotic lesion in a blood vessel, for example, a coronary artery, may be treated by coronary revascularization. Lesions are evaluated prior to treatment to determine its potential effectiveness on blood flow within the coronary artery, for example, visually, by Quantitative Coronary Angiography, or by invasive assessment of the fractional flow reserve (FFR). FFR performed at the time of ICA (invasive coronary angiography) provides an additional functional assessment of stenosis significance as compared to anatomical assessment by ICA. It has been shown to be more effective for revascularization guidance than ICA alone with respect to event-free survival. Stenotic lesions associated with FFR values of 0.80 or less are considered clinically significant (ischemia-causing) and for them revascularization can be beneficial.

FFR may be measured invasively using wires with pressure sensors that are inserted into the blood vessel and across the stenosis. However, equipment to invasively measure the FFR may be not universally available, is generally expensive, and the procedure is time consuming to perform.

Less invasive or non-invasive methods of estimating the FFR have been developed. Some methods rely on imaging to estimate the FFR, for example, using computed tomography (CT) images, and/or invasive angiography images. The estimated FFR computed using imaging methods relies partially on data derived from patient populations, and is therefore less accurate in comparison to invasive FFR measurements.

SUMMARY

According to a first aspect a computer implemented method for calculation of a functional index parameter in at least one blood vessel of a patient, comprises: receiving a dataset of registered functional image data and anatomical image data, wherein the functional image data and the anatomical image data include data indicative of anatomical and functional data for at least one blood vessel of a certain patient; calculating at least one value for at least one functional index parameter for at least one of: (i) at least one blood vessel, and (ii) for the anatomical region of the at least one blood vessel, wherein the at least one value of the at least one functional index parameter is computed based on the functional image data of the dataset; and outputting the calculated at least one value for the at least one functional index parameter for the at least one blood vessel of the certain patient.

According to a second aspect, system for calculation of a functional index parameter in at least one blood vessel of a patient, comprises: a program store storing code; and a processor coupled to the program store for implementing the stored code, the code comprising: code to receive a dataset of registered functional image data and anatomical image data, wherein the functional image data and the anatomical image data include data indicative of anatomical and functional data for at least one blood vessel of a certain patient; code to calculate at least one value for at least one functional index parameter for at least one of: (i) at least one blood vessel, and (ii) for the anatomical region of the at least one blood vessel, wherein the at least one value of the at least one functional index parameter is computed based on the functional image data of the dataset; and code to output the calculated at least one value for the at least one functional index parameter for the at least one blood vessel of the certain patient.

According to a third aspect, a computer program product comprising a non-transitory computer readable storage medium storing program code thereon for implementation by a processor of a system for calculation of a functional index parameter in at least one blood vessel of a patient, comprises: instructions to receive a dataset of registered functional image data and anatomical image data, wherein the functional image data and the anatomical image data include data indicative of anatomical and functional data for at least one blood vessel of a certain patient; instructions to calculate at least one value for at least one functional index parameter for at least one of: (i) at least one blood vessel, and (ii) for the anatomical region of the at least one blood vessel, wherein the at least one value of the at least one functional index parameter is computed based on the functional image data of the dataset; and instructions to output the calculated at least one value for the at least one functional index parameter for the at least one blood vessel of the certain patient.

The systems and/or methods (e.g., stored code executed by processor(s)) described herein relate to the technical problem of improving accuracy of image based calculations of a functional index parameter (e.g., FFR) for an anatomical territory of a blood vessel (e.g., stenotic lesion, optionally of a coronary artery) of a certain patient. The technical problem may include improving the accuracy of calculating the functional index parameter using non-invasive methods, optionally non-invasive imaging methods (it is noted that non-invasive imaging includes injection of contrast and/or radioactive tracers, for example, for a CT scan and/or a SPECT scan).

The systems and/or methods (e.g., stored code executed by processor(s)) described herein improve performance of a computing device and/or computing system (e.g., client terminal and/or server), by reducing the time and/or processing hardware (e.g., memory, processor(s), providing computational efficiency improvements) to calculate the functional index parameter for the certain patient using patient specific nuclear medicine imaging data, rather than, for example, performing additional computations to try and improve the accuracy of an estimated non patient specific functional index parameter using non patient specific data such as based on estimated mathematical relationships and/or using data derived from a large number of patients.

The systems and/or methods (e.g., stored code executed by processor(s)) described herein improve performance of a computing device and/or computing system (e.g., client terminal and/or server), by improving the accuracy of calculating functional index parameter(s) for blood vessel(s) of a certain patient by using functional index parameters extracted from nuclear medicine imaging data of the certain patient, in comparison to other methods that are less accurate due to estimation of the functional index parameters using non patient specific data and/or mathematical relationships.

The systems and/or methods described herein improve performance of existing procedure and/or angiographic equipment, such as x-ray imaging equipment, and operator stations (computing units). For example, by improving the ability to non-invasively identify physiologically significant stenotic lesions that benefit from interventional treatment (e.g., stent placement), the procedure time for treating patients may be reduced, less imaging time may be needed (e.g., reducing the radiation dose to the patient and/or the processing time of the imaging equipment), and/or fewer stents may be required. In another example, the number of invasive measurements performed within the patient is reduced. In one case, no invasive measurements are necessarily performed, based on the estimated values of the functional index parameters calculated using the registered imaging dataset.

In a first possible implementation form of the method or the system or the computer program product according to the first, second, or third aspects, the functional image data is obtained from a nuclear imaging device, selected from the group consisting of: single-photon emission computed tomography (SPECT) machine and positron emission tomography (PET).

In a second possible implementation form of the method or the system or the computer program product according to any of the previous implementation forms of the first, second, or third aspects, functional image data is obtained from a dynamic SPECT machine that outputs data designed to quantify coronary flow.

In a third possible implementation form of the method or the system or the computer program product according to any of the previous implementation forms of the first, second, or third aspects, boundary conditions for the certain patient are calculated using the functional image data of the dataset, and the calculated boundary conditions are used to calculate the at least one value for the at least one functional index parameter for the at least one blood vessel of the certain patient.

In a fourth possible implementation form of the method or the system or the computer program product according to any of the previous implementation forms of the first, second, or third aspects, the functional index parameter is computed for a member selected from the group consisting of: per blood vessel, per stenotic lesion, per blood vessel territory, globally for the heart.

In a fifth possible implementation form of the method or the system or the computer program product according to any of the previous implementation forms of the first, second, or third aspects, the at least one functional index parameter is selected from the group consisting of: tissue perfusion, viability, reversibility, wall motion, wall thickening, flow, flow reserve, and corresponding to fractional flow reserve (FFR).

In a sixth possible implementation form of the method or the system or the computer program product according to any of the previous implementation forms of the first, second, or third aspects, the at least one functional index parameter is computed using one or more machine learning methods.

In a seventh possible implementation form of the method or the system or the computer program product according to any of the previous implementation forms of the first, second, or third aspects, the method or the system or the computer program product further comprise: computing a flow related value using a mathematical model, based on anatomical imaging data of the patient without registered nuclear imaging data; and identifying a mismatch between the flow related value and the at least one value of the functional index parameter, the mismatch potentially indicative of microvascular disease in the at least one vessel.

In an eighth possible implementation form of the method or the system or the computer program product according to the seventh implementation form of the first, second, or third aspects, the method or the system or the computer program product further comprise: adjusting for the mathematical model, at least one parameter denoting resistance of very small vessels of the heart, until the mismatch is eliminated within a mismatch requirement.

In a ninth possible implementation form of the method or the system or the computer program product according to the seventh or eighth implementation form of the first, second, or third aspects, the method or the system or the computer program product further comprise: determining an abnormal value of at least one parameter denoting resistance of very small blood vessels of the heart; setting, for the mathematical model, the at least one parameter denoting resistance of very small blood vessels of the heart to a normal value; computing the flow related values using the mathematical model including the normal value of the at least one parameter denoting resistance of very small blood vessels of the heart; and evaluating whether the computed flow related values denote normal values.

In a tenth possible implementation form of the method or the system or the computer program product according to any of the previous implementation forms of the first, second, or third aspects, the functional index parameter corresponds to a fractional flow reserve (FFR) parameter.

In an eleventh possible implementation form of the method or the system or the computer program product according to any of the previous implementation forms of the first, second, or third aspects, a first functional index parameter is computed for anatomical region of at least one coronary artery when the patient is at rest, a second functional index parameter is computed for the anatomical region of at least one coronary artery during a state of the patient representing maximal blood flow through the at least one coronary artery, and a local coronary flow reserve (CFR) is computed by dividing the second functional index parameter by the first functional index parameter for each of the at least one coronary artery.

In a twelfth possible implementation form of the method or the system or the computer program product according to any of the previous implementation forms of the first, second, or third aspects, calculating comprises using at least one boundary condition as input for a computational fluid dynamics (CFD) mathematical model representing blood flow through the anatomical region of the at least one blood vessel, wherein the CFD mathematical model is analyzed to solve fluid dynamic equations to calculate values corresponding to blood flow.

In a thirteenth possible implementation form of the method or the system or the computer program product according to any of the previous implementation forms of the first, second, or third aspects, the method or the system or the computer program product further comprise: analyzing the value of the functional index parameter for the anatomical region according to a flow requirement to identify a hemodynamically significant stenosis in the at least one anatomical region of the at least one blood vessel.

In a fourteenth possible implementation form of the method or the system or the computer program product according to any of the previous implementation forms of the first, second, or third aspects, the at least one functional index parameter is based on one or more members selected from the group consisting of: absolute myocardial blood flow (MBF), blood flow through the at least one blood vessel, blood flow through at least one coronary vessel, and coronary flow reserve (CFR).

In a fifteenth possible implementation form of the method or the system or the computer program product according to any of the previous implementation forms of the first, second, or third aspects, the calculated at least one value is presented as at least one indication on a graphical user interface (GUI) presenting on a display a three dimensional image of the at least one blood vessel.

In a sixteenth possible implementation form of the method or the system or the computer program product according to any of the previous implementation forms of the first, second, or third aspects, the at least one blood vessel includes a coronary vessel of a heart of the patient.

In a seventeenth possible implementation form of the method or the system or the computer program product according to any of the previous implementation forms of the first, second, or third aspects, the functional index parameter corresponds to a CT-FFR (computed tomography derived fractional flow reserve (FFR)) parameter calculated from coronary CT angiography data.

In an eighteenth possible implementation form of the method or the system or the computer program product according to any of the previous implementation forms of the first, second, or third aspects, the functional index parameter corresponds to a ICA-FFR (interventional coronary angiography) parameter calculated from x-ray angiographic data.

In a nineteenth possible implementation form of the method or the system or the computer program product according to any of the previous implementation forms of the first, second, or third aspects, the functional index parameter is selected from the group consisting of: at least one physiological parameter, and a relationship between at least two physiological parameters.

In a twentieth possible implementation form of the method or the system or the computer program product according to any of the previous implementation forms of the first, second, or third aspects, the functional index parameter is defined for at least one anatomical territory.

In a twenty-first possible implementation form of the method or the system or the computer program product according to any of the previous implementation forms of the first, second, or third aspects, the at least one functional index parameter is extracted during at least one of: a first state of the patient, and a second state of the patient.

In a twenty-second possible implementation form of the method or the system or the computer program product according to any of the previous implementation forms of the first, second, or third aspects, the at least one functional index parameter is calculated based on at least one of the following values value computed based on functional imaging data: coronary flow reserve (CFR), relative CFR, and quantitative SPECT.

In a twenty-third possible implementation form of the method or the system or the computer program product according to any of the previous implementation forms of the first, second, or third aspects, the at least one functional index parameter is calculated based on anatomical geometry of the anatomical region extracted from the functional data.

In a twenty-fourth possible implementation form of the method or the system or the computer program product according to any of the previous implementation forms of the first, second, or third aspects, the method or the system or the computer program product further comprise: calculating the at least one value for the functional index parameter of at least one other vessel located within at least one other anatomical territory external to the at least one anatomical territory.

In a twenty-fifth possible implementation form of the method or the system or the computer program product according to any of the previous implementation forms of the first, second, or third aspects, the at least one functional index parameter is computed per-vessel of the at least one blood vessel, and includes one or more members selected from the group consisting of: MBF, CFR, RFR, and rest flow.

In a twenty-sixth possible implementation form of the method or the system or the computer program product according to any of the previous implementation forms of the first, second, or third aspects, the at least one blood vessel includes at least one stenotic lesion.

In a twenty-seventh possible implementation form of the method or the system or the computer program product according to any of the previous implementation forms of the first, second, or third aspects, the functional image data is obtained from a dynamic SPECT machine that outputs data designed to quantify coronary flow.

In a twenty-eighth possible implementation form of the method or the system or the computer program product according to any of the previous implementation forms of the first, second, or third aspects, the anatomical image data is obtained from an x-ray based imaging machine.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE SEVERAL VIEWS OF THE DRAWINGS

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings.

DETAILED DESCRIPTION

Figure 1:
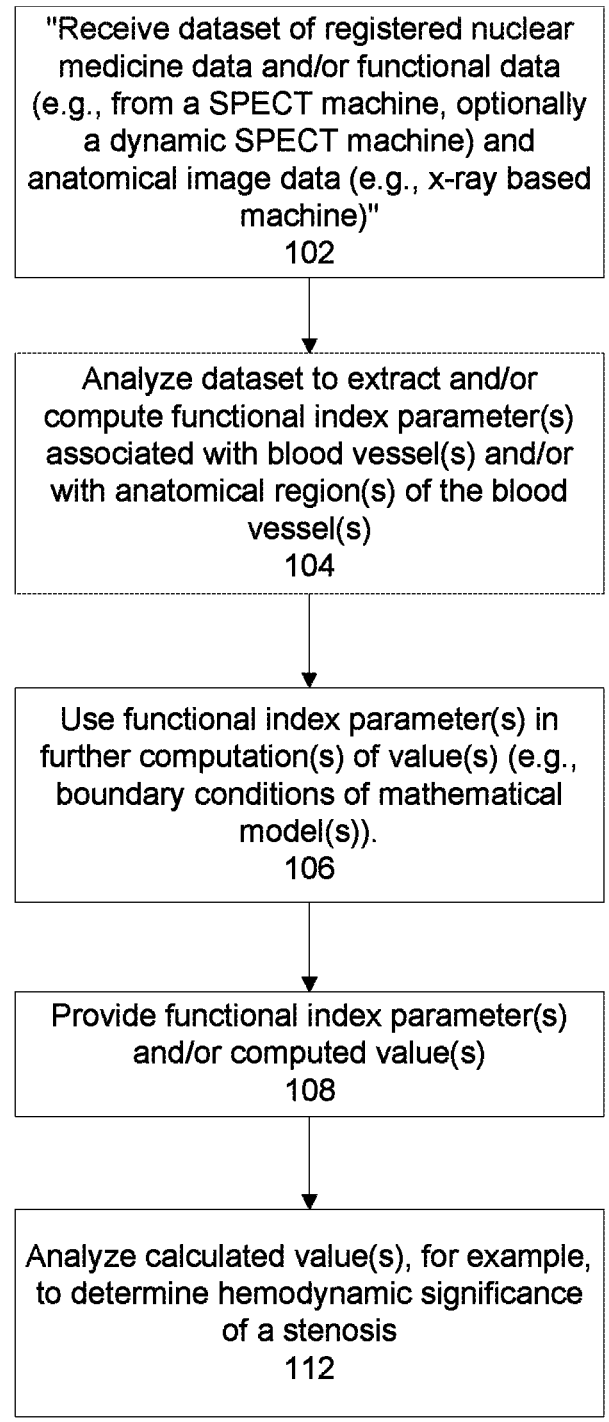
FIG. 1 is a flowchart of a method for estimating value(s) of functional index parameter(s) in one or more blood vessels, or in one or more anatomical territories of one or more blood vessels of a patient using nuclear medicine image data, in accordance with some embodiments of the present invention.

The present invention, in some embodiments thereof, relates to methods and systems for computation of a functional index parameter and, more specifically, but not exclusively, to methods and systems for computation of a functional index parameter of blood vessel(s) of a patient.

An aspect of some embodiments of the present invention relate to systems and/or methods (e.g. code stored in a storage device, executed by processor(s)) that calculate one or more values for one or more functional index parameters associated with blood vessel(s) (which may have a stenotic lesion) using functional imaging data, optionally nuclear medicine image data (optionally obtained from a nuclear medicine device, for example, from a single-photon emission computed tomography (SPECT) machine, optionally a dynamic SPECT machine, and/or positron emission tomography (PET) systems), and/or data obtained from magnetic resonance imaging (MRI) based systems that is registered with anatomical imaging data. Exemplary functional index parameters include: tissue perfusion, viability, reversibility, wall motion, wall thickening, flow, and flow reserve. The functional index parameter(s) are computed, for example, per blood vessel with or without stenotic lesion, across the stenotic lesion, per tissue territory (e.g., myocardium) fed by the blood vessel having the stenotic lesion, and/or globally for the organ (e.g., the heart). The functional index parameter(s) may be used to compute values based on blood flow and/or pressure changes within the blood vessel that occur across the stenotic lesion, optionally corresponding to a fractional flow reserve (FFR) parameter (e.g., correlated with an invasively measured FFR according to a correlation requirement). The functional index parameter(s) may serve as boundary conditions into mathematical model(s) that compute parameters for evaluation of the stenotic lesion, for example, imaged based FFR values. The boundary conditions obtained using functional index parameters represent actual patient specific data.

Optionally, the functional index parameters are estimated using dynamic tomographic SPECT imaging. The functional index parameter may represent, for example, an estimation of global or regional coronary flow or global or regional coronary flow reserve. Functional index parameters representing coronary flow or coronary flow reserve may be provided by a D-SPECT® nuclear medicine machine (available from Spectrum Dynamics Medical, Caesarea, Israel).

Such D-SPECT® nuclear medicine data has higher resolution and sensitivity in comparison to standard SPECT machines. CZT (cadmium zinc telluride) camera allows to overcome the low temporal resolution of conventional scintillation crystals cameras when following rapidly changing concentration of a tracer. For example, each image of the D-SPECT nuclear medicine data provides a snapshot collected over about 1 second to 10 seconds for dynamic scans, or about 1 minute to 10 minutes for perfusion or above 10 minutes, in comparison to SPECT based perfusion imaging that collect data over at least 5 minutes, or at least 10, 20, or 30 minutes. The D-SPECT nuclear medicine dynamic data may be conceptually considered as instantaneous data in comparison to perfusion SPECT data. Quantification of functional index parameter(s) using dynamic data supplies additional information about one or more (e.g., all) myocardial territories and may be beneficial for example, for patients with multi-vessel CAD (coronary artery disease), microvascular disease, and equivocal perfusion findings.

The blood vessel(s) include vessels that may develop stenotic lesions, for example, coronary vessels of the heart, renal arteries, carotid arteries, and femoral arteries. Stenotic lesions may develop due to a variety of reasons, for example, atherosclerosis, post trauma scarring, and fibromuscular dysplasia.

The use of the nuclear medicine image data to provide the functional index parameter(s) improves accuracy of other scores (e.g., FFR) calculated based on anatomical imaging data (e.g., x-ray based imaging, which may be two dimensional (2D) data, for example, from an angiography machine, and/or three dimensional (3D) data, for example, from a CT and/or MRI machine). Improved non-invasive estimation of the functional index parameter(s) allows identification of blood vessel(s) with physiologically significant stenotic lesions, which may be targeted for treatment. For example, scores representing the association between functional index parameters before and after the stenotic lesion may be computed, for example, FFR.

The functional index parameter(s) may be used as boundary conditions that serve as input into a mathematical model, for example, that represents blood flow through the blood vessels of the anatomical imaging data, for example, through one or more coronary vessels. The blood flow may be estimated, for example, by computational fluid dynamic (CFD) methods that solve fluid dynamic equations. The boundary conditions represent patient specific functional values denoting actual state of the blood vessel and/or tissue (e.g., heart myocardium) of the patient. The use of the boundary conditions provides a more accurate patient specific picture of the state of the patient (e.g., FFR values) in comparison to, for example, estimation of boundary conditions using mathematical relationships such as geometry of vessels and/or myocardium, and/or estimation of boundary conditions using generic and/or non-specific data (e.g., average values obtained from a pool of other subjects).

Optionally, a mismatch is identified between a flow related value computed using a mathematical model based on anatomical imaging data without registered SPECT data (representing modeled flow), and value(s) of the functional index parameter (representing actual flow). The mismatch may be indicative, for example, of CMD (coronary microvascular disease). Parameter(s) of the mathematical model denoting resistance of very small vessels of the heart may be adjusted to eliminate the mismatch within a mismatch requirement. The successful elimination of the mismatch by an abnormal value of microvascular resistance may be indicative for the presence of CMD. CMD is treated differently than CAD (by medical therapy rather than stenting or surgery), and its diagnosis is challenging.

Optionally, the blood flow calculated with modified value of microvascular resistance provides an estimation of the effect of treatment of CMD for the patient, for example, using medications (e.g., rather than stenting). When abnormal microvascular resistance is detected based on the identified mismatch, the effects of the therapy of CMD for the patient may be evaluated. The value of the microvascular resistance may be artificially set within normal values (e.g., range) in the mathematical model. The flow in the vessel(s) (e.g., coronary arteries, other larger non-microvascular vessels) may be recalculated using the normal values (e.g., range) of the microvascular resistance. The flow in the vessel(s) may be indicative of the results of treatment of the CMD. When the flow in the vessel(s) denotes a normal value (e.g., flow rate and FFR are determined to fall within a normal range of values), the drug based treatment of the CMD may be determined to be successful. When the flow in the vessel(s) is determined to be abnormal in value (e.g., flow rate or FFR are outside the range), the drug based treatment of the CMD may be determined to be insufficient, and/or incorrect. For example, stenting may be required in addition to, and/or instead of the CMD treatment, and/or the CMD treatment may need adjustment.

As used herein, the term coronary microvascular disease serves as a common example of a diagnosis based on the mismatch in values computed using a mathematical model based on imaging data, and functional index parameters derived from nuclear medicine imaging data of a patient. The term coronary microvascular disease is not meant to be necessarily limiting, and the mismatch together with estimated value of functional index parameter may provide a comprehensive index of severity of cardiac ischemia due to various factors, for example, CAD or CMD.

The systems and/or methods (e.g., stored code executed by processor(s)) described herein relate to the technical problem of improving accuracy of image based calculations of a functional index parameter (e.g., FFR) for an anatomical territory of a blood vessel (e.g., stenotic lesion, optionally of a coronary artery) of a certain patient. The technical problem may include improving the accuracy of calculating the functional index parameter using non-invasive methods, optionally non-invasive imaging methods (it is noted that non-invasive imaging includes injection of contrast and/or radioactive tracers, for example, for a CT scan and/or a SPECT scan).

The systems and/or methods (e.g., stored code executed by processor(s)) described herein improve performance of a computing device and/or computing system (e.g., client terminal and/or server), by reducing the time and/or processing hardware (e.g., memory, processor(s), providing computational efficiency improvements) to calculate the functional index parameter for the certain patient using patient specific nuclear medicine imaging data, rather than, for example, performing additional computations to try and improve the accuracy of an estimated non patient specific functional index parameter using non patient specific data such as based on estimated mathematical relationships and/or using data derived from a large number of patients.

The systems and/or methods (e.g., stored code executed by processor(s)) described herein improve performance of a computing device and/or computing system (e.g., client terminal and/or server), by improving the accuracy of calculating functional index parameter(s) for blood vessel(s) of a certain patient by using functional index parameters extracted from nuclear medicine imaging data of the certain patient, in comparison to other methods that are less accurate due to estimation of the functional index parameters using non patient specific data and/or mathematical relationships.

The systems and/or methods described herein improve performance of existing procedure and/or angiographic equipment, such as x-ray imaging equipment, and operator stations (computing units). For example, by improving the ability to non-invasively identify physiologically significant stenotic lesions that benefit from interventional treatment (e.g., stent placement), the procedure time for treating patients may be reduced, less imaging time may be needed (e.g., reducing the radiation dose to the patient and/or the processing time of the imaging equipment), and/or fewer stents may be required. In another example, the number of invasive measurements performed within the patient is reduced. In one case, no invasive measurements are necessarily performed, based on the estimated values of the functional index parameters calculated using the registered imaging dataset.

Accordingly, the systems and/or methods described herein are inextricably tied to computer technology and/or imaging equipment, to overcome an actual technical problem arising in calculation of functional index parameter(s) for a certain patient.

Before explaining at least one embodiment of the invention in detail, it is to be understood that the invention is not necessarily limited in its application to the details of construction and the arrangement of the components and/or methods set forth in the following description and/or illustrated in the drawings and/or the Examples. The invention is capable of other embodiments or of being practiced or carried out in various ways.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures.

For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

As used herein, the term nuclear medicine image data may sometimes be interchanged with the term functional image data, that is obtained from a nuclear imaging device (for example, SPECT machine or PET), and/or MRI based systems.

As used herein, the term physiological significance (of the stenosis) means degree of stenosis when ischemia is caused, that is, blood flow to the heart muscle is reduced, preventing it from receiving enough oxygen.

As described the term FFR, which may be computed using the functional index parameter(s) obtained from the nuclear medicine component of the registered dataset sometimes means image-based FFR and/or means computed FFR, which represents an estimate of the invasively measured FFR. The image-based FFR and/or computed FFR may be computed using one or more methods, for example, computational fluid mathematical models based on anatomic images. The functional index parameter(s) (which represent actual patient specific data) may serve as boundary conditions for computing the image-based FFR.

Figure 2:
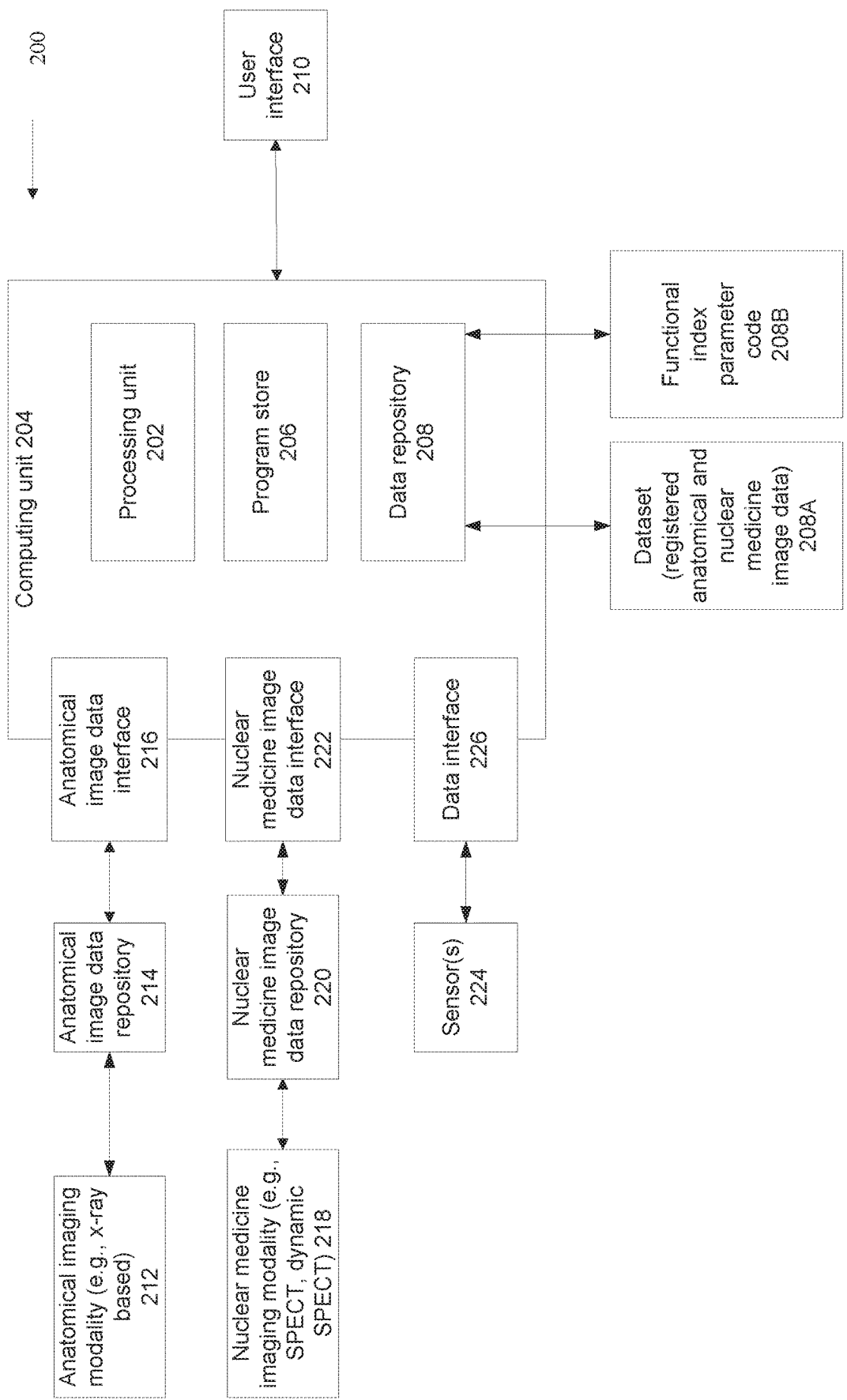
FIG. 2 is a block diagram of components of a system that estimates value(s) of function index parameter(s) using nuclear medicine image data, in accordance with some embodiments of the present invention.

Reference is now made to FIG. 1, which is a flowchart of a method for estimating value(s) of functional index parameter(s) in one or more anatomical territories of one or more blood vessels of a patient using a dataset of registered anatomical and nuclear medicine image data, in accordance with some embodiments of the present invention. Reference is also made to FIG. 2, which is a block diagram of components of a system 200 that estimates value(s) of functional index parameter(s) using the dataset of registered anatomical and nuclear medicine image data, in accordance with some embodiments of the present invention. Components of FIG. 2, may execute one or more acts of the method described with reference to FIG. 1. For example, a processing unit 202 of a computing unit 204 executes code instructions stored in a program store 206.

The systems and/or methods described herein use nuclear medicine image data to calculate functional index parameter(s) or to improve the accuracy of calculated value(s) for functional index parameter(s) for a portion of blood vessel(s). A healthcare worker (e.g., interventional cardiologist, or surgeon) reviewing the calculated value(s) of the functional index parameter(s) may be able to more effectively determine the effect of certain lesions (e.g., stenosis) within vessels (e.g., of the heart) on the function of the target organ (e.g., heart muscle). Based on the calculated value(s), the healthcare worker may better determine which lesion of which vessels to treat, and/or the manner of treatment. For example, certain lesions may appear structurally significant, but the patient may not benefit from interventional treatment.

Computing unit 204 may be implemented as, for example, a radiology workstation, a client terminal, a server, a computing cloud, a web server, a mobile device, a desktop computer, a thin client, a Smartphone, a Tablet computer, a laptop computer, a wearable computer, glasses computer, and a watch computer. Computing unit 204 may include locally stored software that performed one or more of the acts described with reference to FIG. 1, and/or may act as one or more servers (e.g., network server, web server, a computing cloud) that provides services (e.g., one or more of the acts described with reference to FIG. 1) to one or more client terminals, for example, providing software as a service (SaaS) to the client terminal(s), providing an application for local download to the client terminal(s), and/or providing functions using a remote access session to the client terminals, such as through a web browser. For clarity, computing unit 204 is shown as a single component, but it is understood that computing unit 204 may be implemented using other architectures, such as the client-server design.

Processing unit 202 may be implemented, for example, as a central processing unit(s) (CPU), a graphics processing unit(s) (GPU), field programmable gate array(s) (FPGA), digital signal processor(s) (DSP), and application specific integrated circuit(s) (ASIC). Processing unit(s) 202 may include one or more processors (homogenous or heterogeneous), which may be arranged for parallel processing, as clusters and/or as one or more multi core processing units.

Program store 206 stores code instructions implementable by processing unit 202, for example, a random access memory (RAM), read-only memory (ROM), and/or a storage device, for example, non-volatile memory, magnetic media, semiconductor memory devices, hard drive, removable storage, and optical media (e.g., DVD, CD-ROM).

Computing unit 204 may include a data repository 208 for storing data, for example, dataset 208A (which includes anatomical image data registered with nuclear medicine image data, as described herein) and/or functional index parameter code 208B (which calculates one or more values for the functional index parameter(s), as described herein). Data repository 208 may be implemented as, for example, a memory, a local hard-drive, a removable storage unit, an optical disk, a storage device, and/or as a remote server and/or computing cloud (e.g., accessed using a network connection).

Computing unit 204 may include a network interface (not shown) for connecting to a network, for example, one or more of, a network interface card, a wireless interface to connect to a wireless network, a physical interface for connecting to a cable for network connectivity, a virtual interface implemented in software, network communication software providing higher layers of network connectivity, and/or other implementations. Computing unit 204 may access one or more remote servers and/or clients using network, for example, to receive the anatomical image data and/or the nuclear medicine image data for centralized processing.

Computing unit 204 includes or is in communication with a user interface 210 allowing a user to enter data and/or view presented data. Exemplary user interfaces 210 include, for example, one or more of, a touchscreen, a display, a keyboard, a mouse, and voice activated software using speakers and microphone.

Referring now back to FIG. 1, at 102, a dataset of registered nuclear medicine image data and anatomical image data is received by computing unit 204 and optionally stored in data repository 208. Alternatively, computing unit 204 performs the registration based on received anatomical image data and nuclear medicine image data. An exemplary method of registration is described with reference to International Patent Application Publication No. WO2016/120869 "SYSTEMS AND METHODS FOR MEDICAL IMAGE REGISTRATION", assigned to the same assignee of the present application, the contents of which are incorporated herein by reference in their entirety.

The registration of the anatomical image data and nuclear medicine data improves the accuracy of segmentation of the myocardium to territories of the coronary arteries in a patient specific manner. Although guidelines may provide population average segmentation of the myocardium to territories of the coronary arteries, for a high percentage of patients the population averaged, segmentation is incorrect. For example, for the right coronary tree, the mutual position of coronary vessel and myocardial segment has an especially high variability. The registration described herein creates a dataset that associates between functional information obtained from the nuclear medicine images with specific coronary arteries that feed territories. Local functional data is used to evaluate the clinical and/or hemodynamic significance of a stenosis, as described herein.

The dataset and/or anatomical image data and nuclear medicine image data may be received, for example, from a server and/or client (e.g., over the network). Computing unit 204 may provide a centralized service to one or multiple clients. In another example, the anatomical images may be provided by anatomical imaging modality 212 and optionally stored in anatomical image data repository 214. Computing unit 204 may access the anatomical images via anatomical image data interface 216 from anatomical image data repository 214 and/or anatomical imaging modality 212. Nuclear medicine images may be provided by nuclear medicine imaging modality 218 and optionally stored in nuclear medicine image data repository 220. Computing unit 204 may access the nuclear medicine images via nuclear medicine image data interface 222 from nuclear medicine image data repository 220 and/or nuclear medicine imaging modality. The dataset may be computed by computing unit 204 and/or received from an external computing unit (e.g., using a network interface) Nuclear medicine image data may be received from nuclear medicine imaging modality 218 and/or from a nuclear medicine image data repository 220 via a nuclear medicine data interface 222, for example, when computing unit 204 is located within for example, a hospital, clinic, or imaging facility that includes the anatomical and/or nuclear medical imaging modalities.

Exemplary anatomical imaging modality 212 include: an x-ray based imaging system (e.g., a fluoroscopy machine, a standard x-ray machine, a computerized tomography (CT) scanner), a magnetic resonance imaging (MRI) scanner, and an ultrasound machine. The images may be 2D (e.g., x-ray, standard ultrasound), and/or 3D (e.g., CT, MRI, 3D ultrasound).

Exemplary nuclear medicine imaging modality 218 includes a single photon emission computed tomography (SPECT) machine, a D-SPECT® machine available from Spectrum Dynamics Medical, a Biosensors International Group Company, and a positron emission tomography (PET) machine. The image data may be collected as part of a heart imaging procedure, for example, a myocardial perfusion scan, at rest and/or with induced stress.

Anatomical image data repository 214 and/or nuclear medicine image data repository 220 may be implemented, for example, as a storage server, a computing cloud, and a local storage device.

Anatomical image data interface 216 and/or nuclear medicine image data interface 222 may be implemented as a single interface, or independent interfaces. Interfaces 216 and/or 222 may be physical interfaces (e.g., cable connection, port, network interface card, antenna for wireless communication) and/or software interfaces (e.g., higher layer connectivity, virtual ports).

The dataset includes nuclear medicine image data and anatomical image data for a part of a heart including one or more blood vessels and optionally including myocardium of a certain patient. The dataset includes an anatomical map of the blood vessels (e.g., in two or three dimensions) registered with functional data associated with territory of the blood vessels. The functional data is derived from the nuclear medicine image data, for example, represented as triangles in a mesh, where each vertex of the mesh is associated with a functional value measured at the respective location (corresponding to the anatomical region within the patient). Exemplary functional values include: perfusion, flow, flow reserve, and/or other values that may be derived from the nuclear medicine image data.

The anatomical image data includes at least a portion of an organ that includes the blood vessel, for example, the heart, the left ventricle, and the right ventricle. The anatomical image data includes, for example, the coronary vessel tree, the left main coronary artery and/or branches thereof, the right coronary artery and/or branches thereof. The imaging data may be based on contrast enhanced lumens of the vessels. The anatomical image data may include other blood vessels that experience stenosis, for example, carotid arteries (e.g., to evaluate carotid artery stenosis), femoral arteries (e.g., to evaluate intermittent claudication), and renal arteries (e.g., to evaluate renal artery stenosis).

The registration may include a three dimensional transformation that aligns the three dimensional model based on the nuclear medicine image data (e.g., translation and/or rotation) to appear to coincide with the shape of the corresponding organ(s) (e.g., the left ventricle) in one or more anatomical images. The blood vessels may be fully or partially segmented. The center line, length, diameter, area, or other geometrical parameters of the stenosis and/or the rest of the blood vessel tree may be quantified. The segmented blood vessels may be divided into one or more anatomical regions (manually by a user and/or automatically by software) for calculation of value(s) for the functional index parameter(s). The myocardial territory (or other tissue) fed by the target blood vessel and/or stenosis being evaluated may be defined. for example, by a user manually marking the target territory (e.g., using a GUI to mark the territory by one or more points, selection using an enclosed polygon, or other methods), and/or automatically by software. Nuclear medicine based measurements may be quantified for the target territory, for example, one or more of: perfusion, viability, reversibility, wall motion, wall thickening, flow, and flow reserve values.

The anatomical images may be obtained based on a likelihood of the patient having coronary artery (CAD) disease. For example, for patients with high likelihood of CAD, the anatomical images may be obtained from invasive coronary angiography (ICA), since such patients are candidates for ICA as part of the management of the CAD. For patients with intermediate or low risk of CAD, the anatomical images may be obtained from a CT scan, to try and spare the patient from the invasive procedure.

At 104, the dataset is analyzed to extract and/or compute one or more functional index parameters associated with one or more blood vessels (optionally per-vessel), and/or with anatomical region(s) of the one or more blood vessels. Optionally, the functional index parameter(s) is extracted from the nuclear medicine data component of the dataset, which is registered to the corresponding anatomical territory of the blood vessel.

The anatomical territory may be defined manually by the user, for example, the user may manually mark the anatomical territory on an image of the vessel(s), for example, placing a mark, or a box, or a circle, using a graphical user interface (GUI) or other application. The anatomical territory may be defined automatically by software, for example, the dataset may be divided into multiple anatomical territories, for example, according to a segmentation of the blood vessels, according to distances along the blood vessels (e.g., every centimeter or other distance), according to vessel diameter or area, or other methods. Each anatomical territory may be analyzed independently, and/or in parallel, and/or sequentially.

Optionally, the functional index parameter associated with anatomical territory of one or more blood vessels is used as a boundary condition(s) that serve as input into mathematical model describing the blood vessel(s). For example, the boundary condition may represent the total blood flow into the myocardium through one or more blood vessels. The total blood flow may be obtained by integrating the value of the functional index parameter(s) over the territory of one or more vessels. The mathematical model of vessels(s) together with boundary condition(s) may be used to calculate blood flow along the blood vessel(s). Basing on the calculated blood flow the value of image-based FFR may be estimated.

Optionally, the functional index parameter(s) is extracted during one or more states of the patient. The functional index parameter may be extracted during rest, when the heart of the patient is pumping while the patient is resting. The functional index parameter may be extracted during a hyperemic state, for example, when adenosine (or another vasodilator) is administered to the patient. The functional index parameter may be extracted during exercise stress test, for example, when the patient is walking on the treadmill or riding a stationary bicycle.

Optionally, the functional index parameter represents one or more functional values. Exemplary functional index parameters include: myocardial perfusion, tissue perfusion, viability (e.g., of the heart and/or other organ and/or other tissue), reversibility, wall motion (e.g., of the left ventricle, right ventricle, left atrium, and/or right atrium), wall thickness (e.g., of the left ventricle, right ventricle, left atrium, and/or right atrium), absolute myocardial blood flow (MBF), blood flow through the blood vessel(s), blood flow through at least one coronary vessel, coronary flow reserve (CFR, the ratio of blood flow in a stenotic coronary blood vessel during maximal hyperaemia to blood flow in the same blood vessel under resting conditions), relative CFR (the ratio of hyperaemic flow in a stenotic blood vessel to hyperaemic flow in a normal blood vessel). It is noted that the MBF, CFR and relative CFR may be obtained using D-SPECT imaging.

Optionally, the functional index parameter(s) are predicted based on statistical learning methods (e.g., a trained statistical classifier). And the use of the machine learning method.

At 106, the one or more functional index parameters for the anatomical territory of the blood vessel are used in additional calculation of value(s). For example, the functional index parameters are used as the boundary condition(s) in mathematical model(s). In another example, the functional index parameters are used to compute relationships across the stenotic lesion, for example the relationship between blood pressure before and after the stenotic lesion, which is indicative of FFR.

Optionally, additional values based on the functional index parameter(s) are calculated for anatomical region(s) located externally to the defined anatomical territory, and/or for other blood vessels. For example, when the dataset is divided into multiple anatomical territories (e.g., adjacent to each other, optionally with adjacent boundaries), values may be calculated for each anatomical territory.

The functional index parameters, which are obtained from actual functional measurements of the patient from the nuclear medicine imaging data provide more accurate boundary conditions, which provide more accurate values for input into mathematical models, in comparison, for example, to other methods that do not use measurements obtained from nuclear medicine imaging data of the patient being evaluated. Such other methods may estimate boundary conditions, for example, from a pool of other patients (e.g., average values), and/or mathematical estimations based on anatomical imaging data, and/or estimates based on biological principles.

The functional index parameter may be used to compute a relationship between a first state of a patient and a second (or more) state of the patient. The functional index parameter may be used to compute the effects of increased blood flow relative to the rest state. The first state may represent blood flow through the anatomical territory of the blood vessel at rest. The second state may represent hyperemic blood flow through the anatomical territory of the blood vessel, for example, after and/or during administration of a vasodilator. Alternatively or additionally, the second state may represent an increase in blood flow during stress, such as when the patient is exercising.

Optionally, a flow characteristic(s) associated with blood flow through the vessel is computed based on the functional index parameter(s), for example, pressure, and/or flow rate. The flow rate characteristic(s) may be calculated using, for example, one or more of the following: fluid dynamics (CFD) methods, using a reduced order model approach, using an analytical model, and/or predicted based on statistical learning methods (e.g., a trained statistical classifier). The machine learning method(s) may include supervised and/or unsupervised learning methods, for example, neural networks, deep learning, support vector machines, clustering methods, Bayesian networks, rule-based learning methods, and decision tree learning. The statistical learning method(s) may be trained, for example, using data generated by a simulation, using data collected from multiple patients, and/or using data manually corrected by a user.

Optionally, the functional index parameter(s) are used as boundary condition(s) that serve as input for a CFD mathematical model. The CFD model may represent blood flow through the blood vessel(s). The CFD mathematical model may be analyzed and/or solved by solving fluid dynamic equations to calculate the value(s) for the functional index parameter(s).

The functional index parameter may be used to compute a non-invasive calculated parameter corresponding to a fractional flow reserve (FFR) parameter. The functional index parameter may correlate with an invasively measured FFR according to a correlation requirement, for example, representing a statistically and/or clinically insignificant difference. Alternatively or additionally, the functional index parameter is used to compute a CT-FFR (computed tomography derived fractional flow reserve (FFR)) parameter, which may be calculated, for example, from coronary CT angiography data. The functional index parameter may be used as boundary condition(s) used as input for calculating the CT-FFR. Alternatively or additionally, the functional index parameter is used to compute a QCA-FFR (quantitative coronary angiography) parameter calculated from x-ray angiographic data. The functional index parameter may be used as boundary condition(s) used as input for the computational fluid dynamics used in calculating the QCA-FFR. It is noted that other FFR based measures may be computed using the functional index parameter(s).

The functional index parameter(s) may be used to compute a local coronary flow reserve (CFR) for one or more coronary arteries. A first value of the functional index parameter is computed for one or more coronary arteries when the patient is at rest. A second value of the functional index parameter is computed for each coronary artery during a state of the patient representing maximal blood flow through the coronary arteries, for example, in response to administration of a vasodilator. The local CFR is computed by dividing the second value of the functional index parameter by the first value of the functional index parameter for each coronary artery.

At 108, the functional index parameter(s) and/or the values computed based on the functional index parameter(s) (e.g., FFR) for the certain patient is provided. The calculated value(s) and/or functional index parameter(s) may be stored in dataset 208A. The calculated value(s) and/or functional index parameter(s) may be stored in association with one or more anatomical territories and/or with one or more vessels, optionally with all the vessels within the dataset.

The calculated value(s) and/or functional index parameter(s) may be presented on a display (e.g., user interface 210), printed in a report, and/or transmitted to a client terminal for local use, and/or used by another process and/or application.

The calculated value(s) and/or functional index parameter(s) may be presented on the display, for example, as numerical values, as an indication on a GUI presenting an image (e.g., two or three dimensional) of the blood vessels, such as different colors for different values or value ranges of the calculated value. For example, calculated value(s) below a threshold are colored red, and values above the threshold are colored green.

Optionally, at 112, the computed value(s) and/or the functional index parameter(s) is analyzed. The value(s) may be analyzed for one or more anatomical territories, for example, territories identified using anatomical imaging data as being potentially problematic, for example, territories appearing to experience a reduction in blood flow. Alternatively or additionally, the value(s) may be analyzed on more global basis, for example, for multiple anatomical territories of one or more blood vessels, for example, to identify significant reductions in blood flow within the vessel network.

The analysis may be performed according to a flow requirement to identify a physiologically significant stenosis (or other lesion) in the blood vessel(s). The flow requirement may be, for example, a threshold, a range, and/or a function. For example, values of the functional index parameter below a certain threshold may be identified as anatomical territories experiencing a significant reduction in blood flow. Such territories may be treated to increase the blood flow, for example, by insertion of a stent, or other treatment to reduce or remove the stenosis (or other narrowing lesion). The analysis may include comparison of values of various functional index parameters and may provide, for example, a comprehensive index of severity of cardiac ischemia due to various factors.

Figure 3:
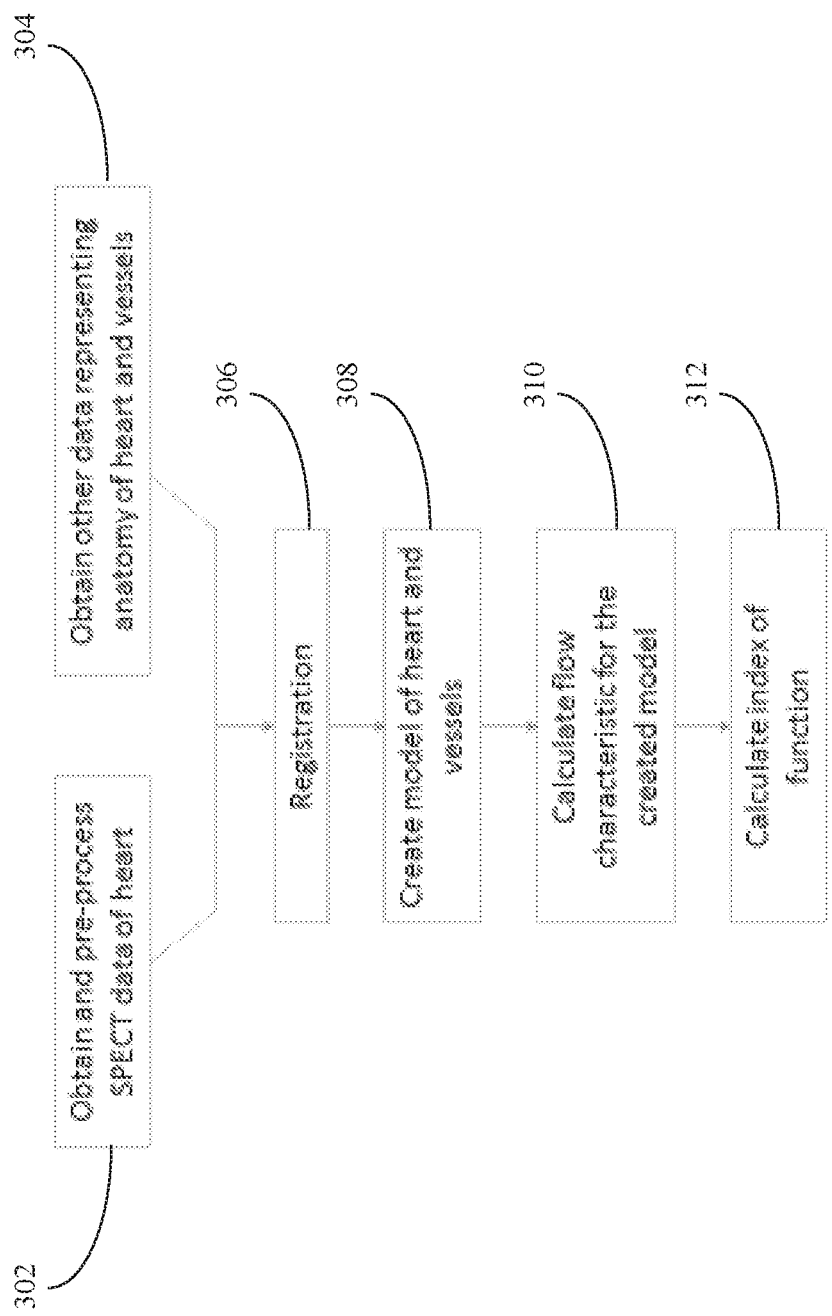
FIG. 3 is a flowchart of another exemplary method for computing value(s) based on the functional index parameter, in accordance with some embodiments of the present invention.

Reference is now made to FIG. 3, which is a flowchart of another exemplary method for computing value(s) based on the functional index parameter, in accordance with some embodiments of the present invention. The method described with reference to FIG. 3 may be implemented using the components of system 200 described with reference to FIG. 2. The method described with reference to FIG. 3 may be a variation of the method (or parts thereof) described with reference to FIG. 1.

At 302, nuclear medicine image data (e.g., SPECT, D-SPECT®) is obtained and optionally pre-processed for registration. The nuclear medicine image data includes data collected for a portion of heart of the patient.

At 304, anatomical imaging data (e.g., CT images, angiographic images) is obtained. The anatomical imaging data includes data collected for the portion of heart including one of more blood vessels of the patient that optionally include a stenotic lesion.

At 306, dataset is created by registering the nuclear medicine image data and the anatomical image data. The dataset of registered images includes a part of the myocardium and the blood vessels with lesion in question.

At 308 a model of the heart and/or other vessels (e.g., coronary, femoral, carotid, renal) is created and/or received. For example, the model may be a computational fluid dynamic model based on equations describing blood flow through the heart and/or vessels. The model may be created based on the anatomical imaging data.

At 310, functional index parameter(s) for the anatomical territory are used to compute flow characteristics for the created model. The functional index parameters are obtained from the nuclear medicine data, and registered to the anatomical territory of the blood vessel with the lesion according to the dataset.

At 312, one or more index of function values are computed using the model and flow characteristics obtained based on the functional index parameters. For example, the index of function values may be image based FFR computations.

Figure 4:
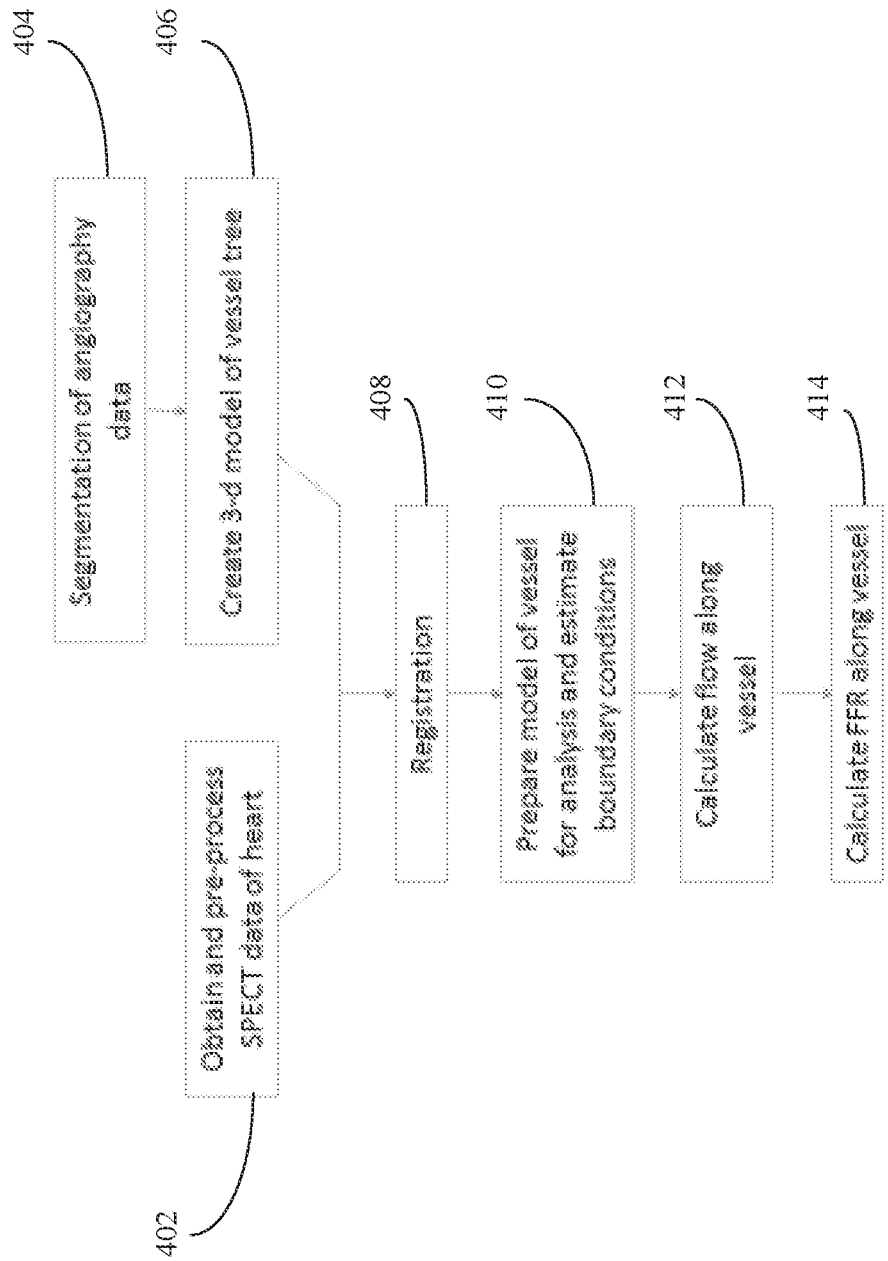
FIG. 4 is a flowchart of another exemplary method for calculating values corresponding to FFR, in accordance with some embodiments of the present invention.

Reference is now made to FIG. 4, which is a flowchart of another exemplary method for calculating values corresponding to FFR using functional index parameters, in accordance with some embodiments of the present invention. The method described with reference to FIG. 4 may be implemented using the components of system 200 described with reference to FIG. 2. The method described with reference to FIG. 4 may be a variation of the method (or parts thereof) described with reference to FIG. 1.

At 402, SPECT image data of a heart of a patient is obtained (e.g., from a SPECT imaging machine) and pre-processed, optionally to calculate one or more functional values used as boundary conditions.

At 404, angiography image data is obtained and segmented to identify the coronary arteries.

Optionally, at 406, a 3D model of the coronary vessel tree is created and/or received. It is noted that registration (performed with reference to block 408) may be performed for angiography data without necessarily creating the 3D model of the vessel tree. Alternatively, registered nuclear medicine image data may be used to create the 3D vessel model.

At 408, the SPECT data and the 3D vessel model are registered to create the dataset. The registration associates functional data from the SPECT with the 3D vessel model.

At 410, a model of the vessels is prepared for analysis and estimation of boundary conditions obtained using the functional index parameters obtained from the SPECT data.

At 412, flow along one or more vessels (e.g., across one or more stenotic lesions being evaluated) is calculated using the functional index parameters.

At 414, the FFR across the stenotic lesion is calculated according to the calculated flow.

Figure 5:
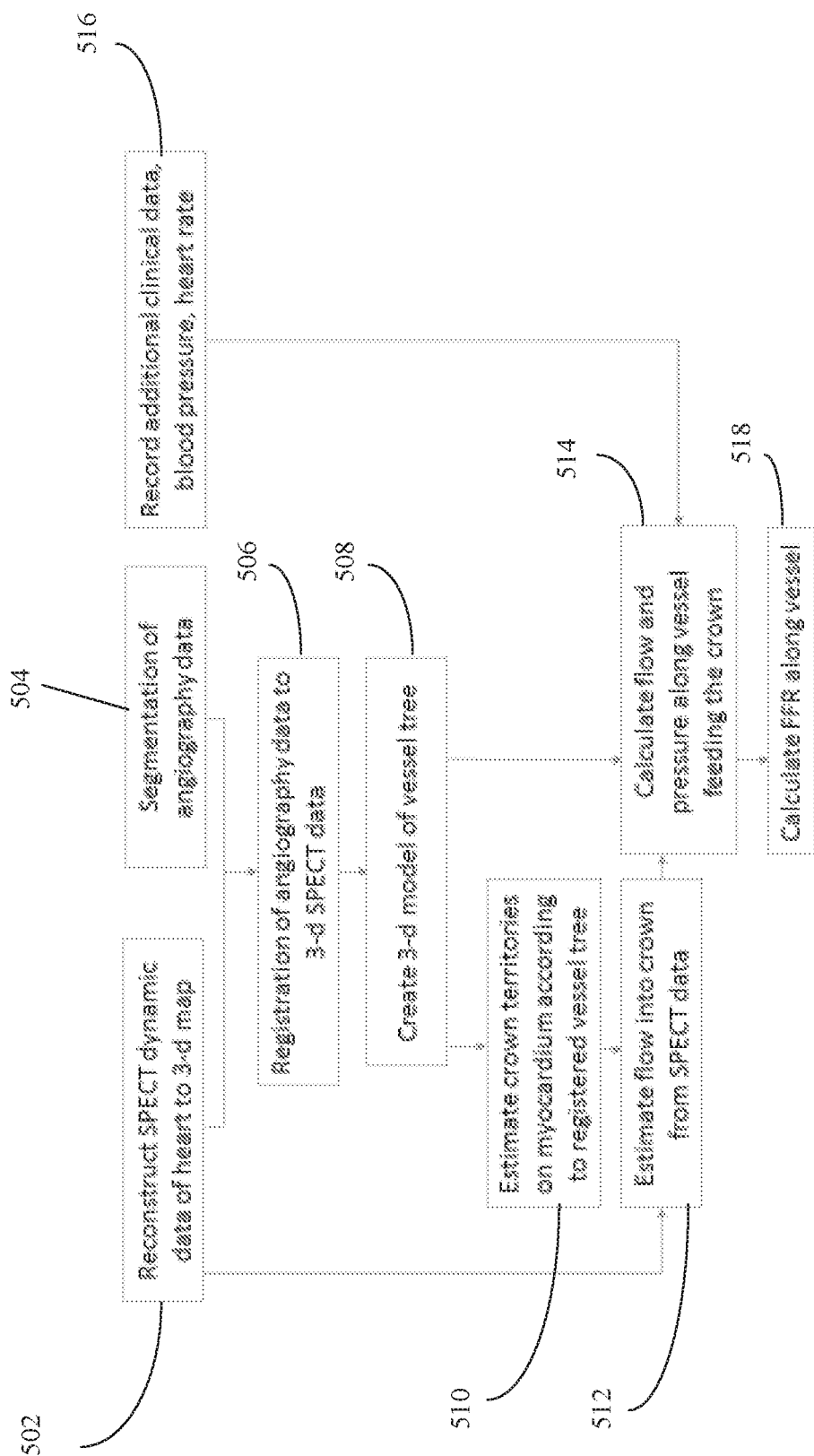
FIG. 5 is a flowchart of yet another exemplary method for calculating values corresponding to FFR, in accordance with some embodiments of the present invention.

Reference is now made to FIG. 5, which is a flowchart of yet another exemplary method for calculating the FFR based on functional index parameter(s), in accordance with some embodiments of the present invention. The method described with reference to FIG. 5 may be implemented using the components of system 200 described with reference to FIG. 2. The method described with reference to FIG. 5 may be a variation of the method (or parts thereof) described with reference to FIG. 1.

At 502, SPECT image data of a heart of a patient is obtained (e.g., from a SPECT imaging machine) and used to create a 3D functional map.

At 504, angiography image data is obtained and segmented to identify the coronary arteries.

At 506, the 3D functional map and the segmented vessels are registered to create the dataset.

At 508, a 3D model of the coronary vessel tree is created based on the registered data, and stored as the dataset.

At 510, crown territories on the myocardium are estimated according to the registered vessel tree (i.e., the dataset).

At 512, the blood flow into each crown territory is estimated from the functional index parameters obtained from the SPECT data component of the dataset.

At 514, the flow and/or pressure values along one or more vessel feeding respective crown territories are calculated using the functional index parameters obtained from the SPECT component of the registered dataset. The flow and/or pressure values and/or may be calculated and/or corrected using additional provided data, for example, additional recorded clinical data, blood pressure, and heart rate.

At 516, additional clinical data of the patient is provided, for example, blood pressure, heart rate, atherosclerotic risk factors, family history of heart disease, smoking statue, and medication use. The clinical data may be extracted from an electronic medical record of the patient, and/or manually entered by a user.

At 518, the FFR along one or more vessels is calculated based on the flow and/or pressure values.

Optionally, the additional clinical data of the patient is considered when computing the FFR along the one or more vessels. For example, blood pressure is used as one of inputs for computation of blood flow in the vessel.

Figure 6:
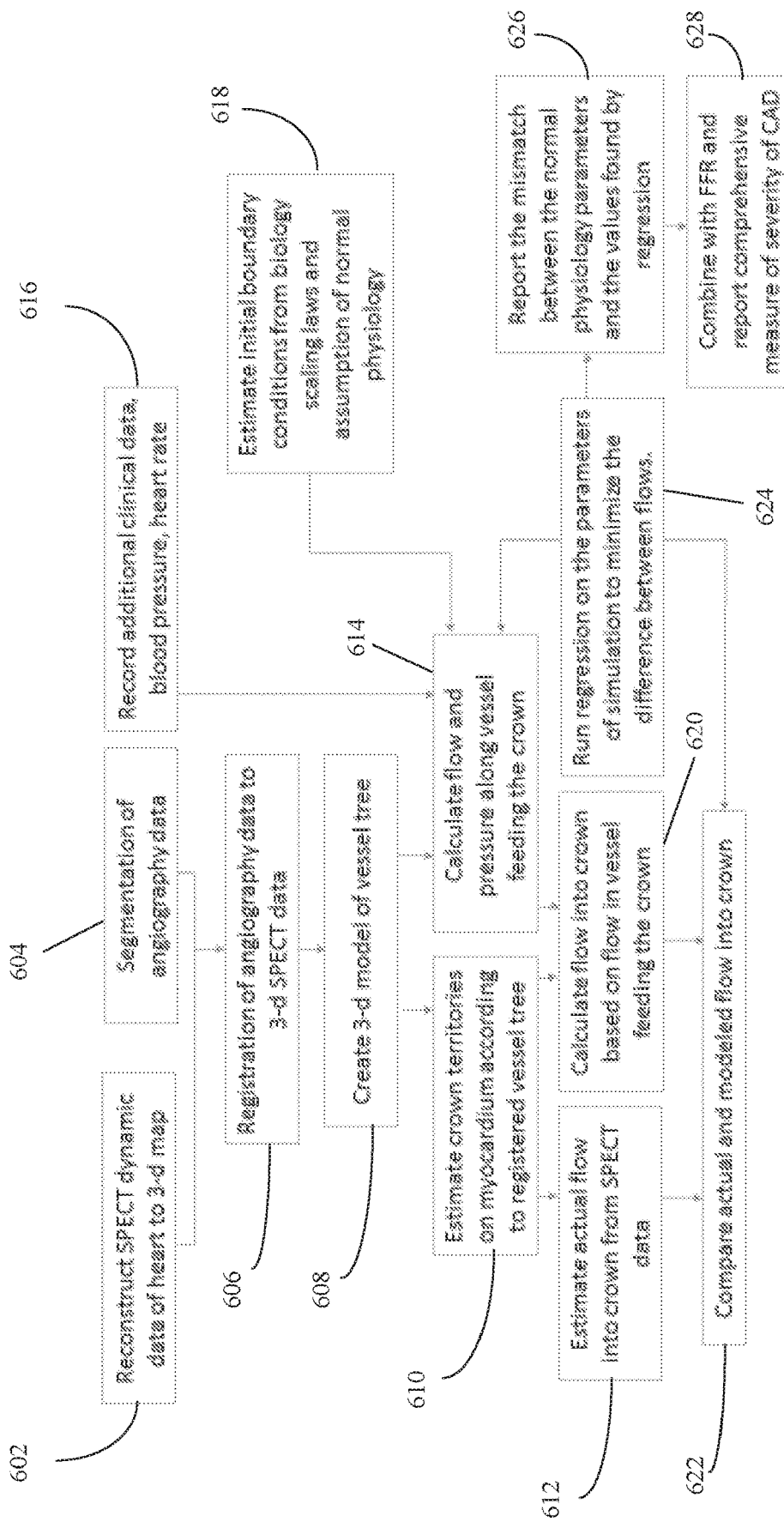
FIG. 6 is a flowchart of an exemplary method for calculating values for a comprehensive index of severity of coronary artery disease according to a mismatch between actual functional index parameter(s) and modeled values, in accordance with some embodiments of the present invention.

Reference is now made to FIG. 6, which is a flowchart of an exemplary method for estimating value of a comprehensive measure of coronary vessel function according to a mismatch between actual functional index parameter(s) and modeled values, in accordance with some embodiments of the present invention. The measure may be indicative of, for example, presence of CMD. The method described with reference to FIG. 6 may be implemented using the components of system 200 described with reference to FIG. 2. The method described with reference to FIG. 6 may be a variation of the method (or parts thereof) described with reference to FIG. 1.

Microvascular disease may be diagnosed when coronary vessels appear anatomically normal, without stenosis visible on anatomical images, but the patient experiences chest pain and/or other symptoms suggestive of decreased blood flow through the vessels of the heart. Microvascular disease results in a damage of very small branches of arteries. Damage to small coronary arteries causes increased resistance to flow in these arteries and decrease of blood flow to heart muscle.

The systems and/or methods described herein may help to detect microvascular disease based on a mismatch between a flow related value computed using a mathematical model based on anatomical imaging without functional data from nuclear imaging, and actual blood flow computed using the functional index parameters. When the flow (determined from the imaging data and/or model) in the coronary vessel is determined to be in the normal range, but the actual flow based on the functional index parameters is indicative of significantly abnormally reduced flow, microvascular disease may be suspected. The model used to compute the FFR may be corrected by adjusting parameters indicative of flow resistance of the very small vessels. The corrected model may be used to simulate the effectiveness of treatment using vasodilator medications (and/or other pharmaceuticals that reduce the resistance in the very small vessels). The adjusted model parameters may complement the estimated value of functional index parameter to provide a comprehensive, optionally multi-dimensional, index characterizing the severity of cardiac ischemia due to various factors.

Blocks 602-616 correspond to blocks 502-516 described with reference to FIG. 6.

At block 618, initial boundary conditions are estimated from biology scaling laws and assumption of normal physiology. The initial boundary conditions are used to calculate the flow and/or pressure along one or more vessels feeding respective crown territories, as described with reference to block 614.

At 620, the flow into one or more crown territories is calculated based on the calculated flow in the respective feeding vessel (which has been calculated using the estimated initial boundary conditions). The flow may be computed using computational fluid dynamic models, and/or other algorithms for computing FFR representations from anatomical imaging data.

At 622, the actual measured flow determined using the functional index parameters obtained from the nuclear medicine data, and the calculated estimated model flow into one or more crown territories are compared to determine the presence of a mismatch. The mismatch may be defined according to a mismatch requirement indicative of statistical error of the measured functional index parameters and/or the computed flow.

At 624, a regression method is run on the simulation parameters to reduce (e.g., minimize) the mismatch between the actual measured flow (using the functional index parameters) and the calculated flow (computed using the mathematical model). The regression method may adjust parameter(s) denoting peripheral resistance of the very small blood vessels of the heart. Blocks 614, 620, 622, and 624 may be iterated, for example, until the mismatch is reduced according to the mismatch requirement (e.g., threshold, range, function).

Microvascular disease may be suspected when the adjustment of the resistance value of the very small blood vessels of the heart in the mathematical model results in elimination of the mismatch. The successful elimination of the mismatch may indicate that the underlying cause of the mismatch is due to high resistance of the very small blood vessels of the heart, and potentially treatable using pharmacologic vasodilators (and untreatable using a stent placed inside the coronary artery).

At 626, the mismatch between the normal physiology parameters and the adjusted values found using the regression method is provided. The amount of mismatch may indicate the severity of the resistance of the very small blood vessels of the heart, suggesting the dose and/or type of medication for treatment.

At 628, the adjusted values are combined with the calculated FFR and reported. The FFR and adjusted values may be used to determine the severity of coronary artery disease (CAD) or microvascular disease in the patient. Treatment using a stent for CAD or using drugs for microvascular disease may be selected accordingly.

Figure 7:
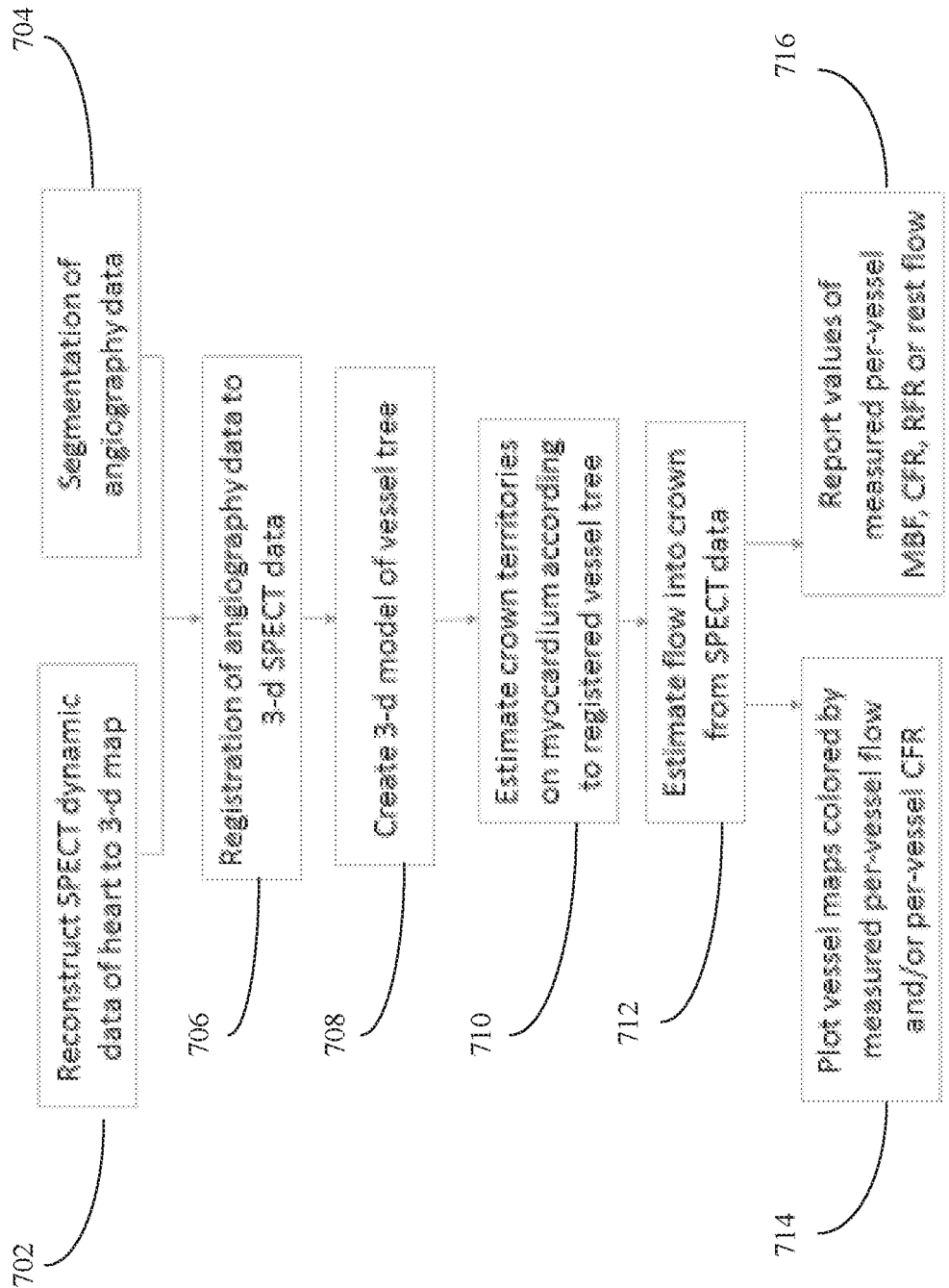
FIG. 7 is a flowchart of an exemplary method of computing and/or displaying per-vessel CFR and/or per-vessel flow for a geometry of a vessel tree, in accordance with some embodiments of the present invention.

Reference is now made to FIG. 7, which is a flowchart of an exemplary method of computing and/or displaying per-vessel CFR (and/or other parameters) and/or per-vessel flow for a geometry of a vessel tree of a certain patient, in accordance with some embodiments of the present invention. The method described with reference to FIG. 7 may be implemented using the components of system 200 described with reference to FIG. 2. The method described with reference to FIG. 7 may be a variation of the method (or parts thereof) described with reference to FIG. 1.

At 702, SPECT image data of a heart of a patient is obtained (e.g., from a SPECT imaging machine) and used to create a 3D functional map.

At 704, angiography image data is obtained and segmented to identify the coronary arteries.

At 706, the 3D functional map and the segmented vessels are registered to create the dataset.

At 708, a 3D model of the coronary vessel tree is created based on the registered data, and stored as the dataset.

At 710, crown territories on the myocardium are estimated according to the registered vessel tree (i.e., the dataset).

At 712, the blood flow into each crown territory is estimated from the functional index parameters obtained from the SPECT data component of the dataset.

At 714, vessel map(s) colored based on measured per-vessel flow and/or per-vessel CFR are plotted and/or rendered and provided for presentation on a display. For example, different colors may be indicative of a scale of the intensity of the flow and/or CFR computed for each vessel. Alternatively or additionally at 716, values(s) of the measured per-vessel MBF, CFR, relative flow reserve (RFR), and/or rest flow are computed (as described herein) and provided, for example, stored in the electronic medical record of the patient, presented on a display for viewing by the physician, and/or forwarded to a remote server and/or client terminal for remote storage and/or presentation.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments disclosed herein.

It is expected that during the life of a patent maturing from this application many relevant anatomical and nuclear medicine imaging modalities will be developed and the scope of the terms anatomical and nuclear medicine image data are intended to include all such new technologies a priori.

As used herein the term "about" refers to ±10%.

The terms "comprises", "comprising", "includes", "including", "having" and their conjugates mean "including but not limited to". This term encompasses the terms "consisting of" and "consisting essentially of".

The phrase "consisting essentially of" means that the composition or method may include additional ingredients and/or steps, but only if the additional ingredients and/or steps do not materially alter the basic and novel characteristics of the claimed composition or method.

As used herein, the singular form "a", "an" and "the" include plural references unless the context clearly dictates otherwise. For example, the term "a compound" or "at least one compound" may include a plurality of compounds, including mixtures thereof.

The word "exemplary" is used herein to mean "serving as an example, instance or illustration". Any embodiment described as "exemplary" is not necessarily to be construed as preferred or advantageous over other embodiments and/or to exclude the incorporation of features from other embodiments.

The word "optionally" is used herein to mean "is provided in some embodiments and not provided in other embodiments". Any particular embodiment of the invention may include a plurality of "optional" features unless such features conflict.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. A computer implemented method for calculation of a functional index parameter in at least one blood vessel of a patient, comprising: receiving, by a processor, a dataset of registered functional image data and anatomical image data, wherein the functional image data and the anatomical image data include data indicative of anatomical and functional data for at least one blood vessel of a certain patient; calculating, by the processor, at least one value for at least one functional index parameter based on the functional image data of the dataset, for at least one of: (i) at least one blood vessel, and (ii) for the anatomical region of the at least one blood vessel; outputting, by the processor, the calculated at least one value for the at least one functional index parameter for the at least one blood vessel of the certain patient; computing, by the processor, a flow related value using a mathematical model, based on anatomical imaging data of the patient without registered nuclear imaging data; and identifying, by the processor, a mismatch between the flow related value and the at least one value of the functional index parameter, the mismatch potentially indicative of microvascular disease in the at least one vessel.

2. The method of claim 1, wherein the functional image data is received by the processor is obtained from a nuclear imaging device, selected from the group consisting of: single-photon emission computed tomography (SPECT) machine, positron emission tomography (PET), and a dynamic SPECT machine that outputs data designed to quantify coronary flow.

3. The computer implemented method of claim 1, wherein boundary conditions for the certain patient are calculated by the processor using the functional image data of the dataset, and the calculated boundary conditions are used to calculate the at least one value for the at least one functional index parameter for the at least one blood vessel of the certain patient.

4. The computer implemented method of claim 1, wherein the at least one functional index parameter is defined for at least one anatomical territory and computed by the processor for a member selected from the group consisting of: per blood vessel, per stenotic lesion, per blood vessel territory, globally for the heart, and wherein the at least one functional index parameter is selected from the group consisting of:

tissue perfusion, viability, reversibility, wall motion, wall thickening, flow, flow reserve, and corresponding to fractional flow reserve (FFR).

5. The computer implemented method of claim 1, further comprising:
adjusting for the mathematical model, by the processor, at least one parameter denoting resistance of very small vessels of the heart, until the mismatch is eliminated within a mismatch requirement.

6. The computer implemented method of claim 1, further comprising:
determining, by the processor, an abnormal value of at least one parameter denoting resistance of very small blood vessels of the heart;
setting by the processor, for the mathematical model, the at least one parameter denoting resistance of very small blood vessels of the heart to a normal value;
computing, by the processor, the flow related values using the mathematical model including the normal value of the at least one parameter denoting resistance of very small blood vessels of the heart; and
evaluating, by the processor, whether the computed flow related values denote normal values.

7. The method of claim 1, wherein a first functional index parameter is computed by the processor for anatomical region of at least one coronary artery when the patient is at rest, a second functional index parameter is computed by the processor for the anatomical region of at least one coronary artery during a state of the patient representing maximal blood flow through the at least one coronary artery, and a local coronary flow reserve (CFR) is computed by the processor by dividing the second functional index parameter by the first functional index parameter for each of the at least one coronary artery.

8. The method of claim 1, wherein calculating comprises using at least one boundary condition as input for a computational fluid dynamics (CFD) mathematical model representing blood flow through the anatomical region of the at least one blood vessel, wherein the CFD mathematical model is analyzed to solve fluid dynamic equations to calculate values corresponding to blood flow.

9. The method of claim 1, further comprising analyzing by the processor, the value of the functional index parameter for the anatomical region according to a flow requirement to identify a hemodynamically significant stenosis in the at least one anatomical region of the at least one blood vessel.

10. The method of claim 1, wherein the at least one functional index parameter is based on one or more members selected from the group consisting of: absolute myocardial blood flow (MBF), blood flow through the at least one blood vessel, blood flow through at least one coronary vessel, and coronary flow reserve (CFR).

11. The method of claim 1, wherein the functional index parameter corresponds to at least one member selected from the group consisting of: a fractional flow reserve (FFR) parameter, a CT-FFR (computed tomography derived fractional flow reserve (FFR)) parameter calculated from coronary CT angiography data, and a ICA-FFR (interventional coronary angiography) parameter calculated from x-ray angiographic data.

12. The method of claim 1, wherein the functional index parameter is selected from the group consisting of: at least one physiological parameter, and a relationship between at least two physiological parameters.

13. The method of claim 1, wherein the at least one functional index parameter is calculated by the processor based on at least one of the following values computed based on functional imaging data: coronary flow reserve (CFR), relative CFR, and quantitative SPECT.

14. The method of claim 1, wherein the at least one functional index parameter is within the anatomical and calculated based on anatomical geometry of the anatomical region extracted from the functional data.

15. The method of claim 1, further comprising calculating by the processor, the at least one value for the functional index parameter of at least one other vessel located within at least one other anatomical territory external to the at least one anatomical territory.

16. The method of claim 1, wherein the at least one functional index parameter is computed by the processor, per-vessel of the at least one blood vessel, and includes one or more members selected from the group consisting of: MBF, CFR, RFR, and rest flow.

17. A system for calculation of a functional index parameter in at least one blood vessel of a patient, comprising:
a non-transitory memory having stored thereon a code; and
a processor coupled to the memory for implementing the stored code, the code comprising:
code to receive a dataset of registered functional image data and anatomical image data, wherein the functional image data and the anatomical image data include data indicative of anatomical and functional data for at least one blood vessel of a certain patient;
code to calculate at least one value for at least one functional index parameter based on the functional image data of the dataset, for at least one of: (i) at least one blood vessel, and (ii) for the anatomical region of the at least one blood vessel;
code to output the calculated at least one value for the at least one functional index parameter for the at least one blood vessel of the certain patient;
code to compute a flow related value using a mathematical model, based on anatomical imaging data of the patient without registered nuclear imaging data; and
code to identify a mismatch between the flow related value and the at least one value of the functional index parameter, the mismatch potentially indicative of microvascular disease in the at least one vessel.

18. The system of claim 17, wherein the anatomical image data is obtained from an x-ray based imaging machine.

19. A computer program product for calculation of a functional index parameter in at least one blood vessel of a patient, comprising:
a non-transitory memory having stored thereon a code which, when executed by a processor, cause the processor to perform:
receiving a dataset of registered functional image data and anatomical image data, wherein the functional image data and the anatomical image data include data indicative of anatomical and functional data for at least one blood vessel of a certain patient;
calculating at least one value for at least one functional index parameter based on the functional image data of the dataset, for at least one of: (i) at least one blood vessel, and (ii) for the anatomical region of the at least one blood vessel;
outputting the calculated at least one value for the at least one functional index parameter for the at least one blood vessel of the certain patient;
computing a flow related value using a mathematical model, based on anatomical imaging data of the patient without registered nuclear imaging data; and identifying a mismatch between the flow related value and the at least one value of the functional index parameter, the mismatch potentially indicative of microvascular disease in the at least one vessel.

\* \* \* \* \*